United States Patent [19]

Wong et al.

[11] Patent Number: 5,038,039

[45] Date of Patent: Aug. 6, 1991

[54] METHOD OF DETECTING THE PRESENCE OF ANOMALIES IN BIOLOGICAL TISSUES AND CELLS IN NATURAL AND CULTURED FORM BY INFRARED SPECTROSCOPY

[75] Inventors: Patrick T. T. Wong, Ottawa, Canada; Basil Rigas, White Plains, N.Y.

[73] Assignees: Cornell Research Foundation, Inc., Ithaca, N.Y.; National Research Council of Canada, Ottawa, Canada

[21] Appl. No.: 478,581

[22] Filed: Feb. 12, 1990

Related U.S. Application Data

[63] Continuation-in-part of Ser. No. 468,721, Jan. 24, 1990, abandoned.

[30] Foreign Application Priority Data

Jan. 29, 1990 [CA] Canada ................................. 2008831

[51] Int. Cl.$^5$ .......................... G01N 21/64; G01J 5/00
[52] U.S. Cl. .................................. 250/339; 250/341; 250/343
[58] Field of Search ....................... 250/339, 341, 343; 128/633

[56] References Cited

U.S. PATENT DOCUMENTS

| | | | |
|---|---|---|---|
| 3,267,932 | 8/1966 | Valliere | 128/675 |
| 3,279,460 | 10/1966 | Sheldon | 128/6 |
| 3,327,119 | 6/1967 | Kamentsky | 250/461.2 |
| 3,456,641 | 7/1969 | Yokota | 128/4 |
| 3,497,690 | 2/1970 | Wheeless | 250/461.2 |
| 3,877,818 | 4/1975 | Burton | 356/416 |
| 4,063,892 | 12/1977 | Vassilev | 436/64 |
| 4,102,646 | 7/1978 | Sleeter | 250/338.1 |
| 4,247,773 | 1/1981 | Nexo | 250/339 |
| 4,273,442 | 6/1981 | Lubbers | 356/326 |
| 4,447,725 | 5/1984 | Biggs | 250/339 |
| 4,481,418 | 11/1984 | Vanzetti | 250/338.1 |
| 4,515,165 | 5/1985 | Carroll | 128/664 |
| 4,623,793 | 11/1986 | Hofke | 250/341 |
| 4,633,087 | 12/1986 | Rosenthal | 250/341 |
| 4,642,778 | 2/1987 | Hieftje et al. | 364/498 |
| 4,649,275 | 3/1987 | Nelson | 250/358.1 |
| 4,707,605 | 11/1987 | Asteimer | 250/347 |
| 4,767,717 | 8/1988 | Baisden | 436/64 |
| 4,767,928 | 8/1988 | Nelson | 250/341 |
| 4,771,176 | 9/1988 | Schiefer | 250/339 |
| 4,807,637 | 2/1989 | Bjorkholm | 128/664 |
| 4,831,258 | 5/1989 | Paulk | 250/349 |

FOREIGN PATENT DOCUMENTS

| | | | |
|---|---|---|---|
| 64-88340 | 4/1989 | Japan | 250/339 |
| 742776 | 6/1980 | U.S.S.R. | 250/339 |
| 2126717 | 3/1984 | United Kingdom | 128/633 |
| 8404665 | 12/1984 | World Int. Prop. O. | 128/633 |

OTHER PUBLICATIONS

Siminovitch D. J. et al., "High Pressure Infrared Spectroscopy of Lipid Bilayers: New Tests for Interdigitation" Biochemia et Biophysica ACTA, vol. 900 (1987) pp. 163-167.

Atanasov, A. G. et al., "Infrared Spectroscopy and Optical Rotatory Dispersion of Liver Mitochondria of Intact and Tumor-Bearing Rats"—Abstract—Biology Pochvoved vol. 26, No. 2 (1971), pp. 8-11.

Wong, Patrick, T. T., et al., Biochemical and Biophysical Research Communications, 146, No. 1, pp. 232-238 (7/87).

*Primary Examiner*—Constantine Hannaher
*Assistant Examiner*—Jacob M. Eisenberg

[57] ABSTRACT

The presence of anomalies in biological tissues and cells in natural and cultured form (e.g. cancerous tissues or cells) is detected by infrared spectroscopy. A beam of infrared light is directed at a sample of tissues or cells in natural or cultured form containing the cells to be tested, and the anomaly is detected at at least one range of frequencies by determining whether changes in infrared absorption have occurred due to the vibration of at least one functional group of molecules present in the sample which is characteristic of the anomaly.

16 Claims, 6 Drawing Sheets

OTHER PUBLICATIONS

Mushayakarara, E. C. et al., "Detection by High Pressure Infrared Spectrometry of Hydrogen-Bonding between Water and Triacetyl Glycerol" Biochemical and Biophysical Research Communications, vol. 134, No. 1 (Jan. 14, 1986) pp. 140–45.

Mushayakarara, E. C. et al., "The Effect of Pressure on the Hydrogen Bonding between Carbonyl and Hydroxy Moieties in 1,2-Dipalmitoylglycerol: A Fourier-Transformation Infrared Spectroscopy Study" Biochemia et Biophysica Acta, vol. 857 (1986) pp. 259.

Andreoli, S. P., et al., The Journal of Pediatrics, 8/86, pp. 292–297.

Jimbow, K., Cancer Research 44, 1128–1134, (3/84).

Kasama, K., The Journal of Biological Chemistry, 264, No. 16, pp. 9453–9461 (6/89).

Lauer, J. L., et al., Proceedings of the 7th New Eng. Biorg. Conf., Troy, NY (3/79).

Rougereau, A., et al., Internat. J. Vit. Nutr. Res. 57 (1987), 19–23.

METHOD OF DETECTING THE PRESENCE OF ANOMALIES IN BIOLOGICAL TISSUES AND CELLS IN NATURAL AND CULTURED FORM BY INFRARED SPECTROSCOPY

CROSS-REFERENCE TO RELATED APPLICATIONS

This is a continuation-in-part of Wong et al. U.S. Ser. No. 07/468,721, filed Jan. 24, 1990, now abandoned.

BACKGROUND OF THE INVENTION

1. Field of the Invention

This invention relates to a method of detecting the presence of anomalies in biological tissues and cells in natural or cultured form by infrared spectroscopy.

Detection of malignancy in mammalian tissue is usually accomplished by obtaining tissue samples by microtone sectioning, followed by histological examination of the samples. Such examination,
i) requires highly skilled examination by a pathologist or other skilled personnel,
ii) is not always reliable, and
iii) it is difficult to detect malignancy in tissue in the early stages.

It has been proposed in U.S. Pat. No. 4,515,165, dated May 7, 1985, "Apparatus and Method for Detecting Tumors" R. Carroll, to detect cancerous tumors by scanning a test region in the body with infrared light having a wavelength 700 to 4,000 nanometers and measuring the amount of absorption and scatter in a scanning mode to produce a shadowgraph image using either single wavelength grey scale or preferably multispectral multiple wavelength false color imaging.

While the proposals of Carroll are useful, the interpretation of the shadowgraph image;
i) has to be carried out by skilled personnel,
ii) is not completely reliable, and
iii) cannot detect malignancy in tissue in the early stages.

There is a need for a method of detecting the presence of anomalies in biological tissues or cells, particularly the malignancy in mammalian tissues or cells, by infrared spectroscopy wherein;
i) interpretation of the tests results can be carried out by personal having no medical skills and after a relatively simple course of training,
ii) with proper care, interpretation of the test results in completely reliable, and
iii) malignancy in tissues or cells can be detected in the early stages.

2. Description of Related Art

It has already been proposed in Russian Patent No. 742,776, to measure the rate of occurrence of wilt by taking infrared spectra of samples of dried, three day old, sprouts of cotton plants, in the frequency region of 900–1,500 cm$^{-1}$, and compare the spectra with a standard spectrum obtained from resistant seeds sprouted in laboratory conditions free from infection.

While the process described in Russian Patent No. 742,776 is useful, taking a sample at random from a mass of dried sprouts has the disadvantage that the sample may not be truly representative of the rate of occurrence, or for that matter, any occurrence, of disease in the original sprouts. Furthermore, there is a danger that the nature of the tissue containing wilt can be changed by the drying process. Thus the comparison of samples of dried sprouts can lead to misleading results.

There is a need for a process for determining the presence of anomalies in biological tissue in the natural form whereby any misinterpretation which may be due to processing the tissue from its natural form is avoided.

SUMMARY OF THE INVENTION

According to the present invention there is provided a method of detecting the presence of anomalies in biological tissues or cells in natural or cultured form by infrared spectroscopy, comprising:
a) directing a beam of infrared light at a sample of the tissues or cells in natural or cultured form, and
b) determining, by spectroscopic analysis, whether variation in infrared absorption occurs in the sample, at at least one range of frequencies, due to the vibration of at least one functional group of molecules present in the sample which is characteristic of that anomaly.

In this specification the expression "biological tissue or cells in natural or cultured form" means biological tissue or cells as they occur in nature or as they may be cultured, and includes tissue or cells which, have been mashed, dispersed in water or sliced, but remain in the natural or cultured form.

The anomaly may be a tissue or cell anomaly.

The anomaly can be due to the presence of malignancy in tissue.

The beam of infrared light may be passed through the samples in an optical interference free manner, and the infrared absorption may be determined by the transmittance characteristics of the sample.

The spectroscopic analysis may be carried out with the samples subjected to high pressure to render readily detectable the infrared absorption characteristic of the said at least one functional group.

The spectroscopic analysis may be carried out, by subjecting the sample to at least two different pressures to render the infrared absorption characteristic detectable by frequency shift.

The spectroscopic analysis may be carried out by subjecting the sample to at least two different pressures to render the infrared absorption characteristic detectable by intensity change.

The said at least one functional group may be a $CH_3$ group.

The said at least one functional group may comprise a $C=O$ group.

The said at least one functional group may be a $CH_2$ group.

The $C=O$ group may be in a membrane lipid.

The tissue may be liver tissue, and the said anomaly is an indication of the presence of cirrhosis in the liver tissue.

The tissue may be thymus tissue, and the said anomaly is an indication of the length of time at room temperature that has passed since that thymus tissue was removed from a patient.

The cells may be human colon epithelial cells.

The tissue may be colon tumor tissue and the said anomaly is an indication of malignancy in said tissue.

The tissue may be liver tumor tissue and the said anomaly is an indication of malignancy in said tissue.

BRIEF DESCRIPTION OF THE DRAWINGS

In the accompanying drawings which illustrate, by way of example, embodiments of the present invention.

DETAILED DESCRIPTION

Figure 1:
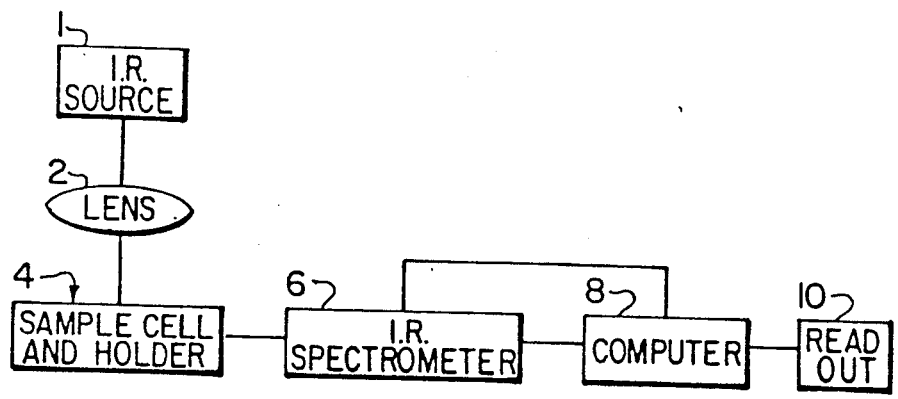
FIG. 1 is a block diagram of an apparatus for detecting the presence of biological tissue anomalies by infrared spectroscopy.

Referring now to FIG. 1, there is shown an infrared source 1, a lens 2, a sample cell and holder 4, an infrared spectrometer 6, a computer 8 and a readout 10.

In operation, a tissue or a cell sample is placed in the sample cell of the sample cell and holder 4 and a beam of infrared light from the source 1 which has been condensed by the lens 2, is passed through the sample in the sample cell and holder 4. Any infrared absorption by an anomaly in the tissue or cell sample is detected by the infrared spectrometer 6, which in turn is computed by the computer to give a readout at the readout 10.

The sample in the sample cell may be, for example tissue which has been, mashed, dispersed in water, or sliced and used in the natural form for the detection of cancerous cells.

Using mashed or water dispersed tissue is not only time consuming but requires that a number of tests be done on different portions of the mashed or water dispersed tissue in order to ensure that the portion containing cancerous cells has not escaped detection.

Using sliced tissue in natural form is less time consuming and more reliable. However, a problem exists with sliced tissue in that optical interference can make the infrared absorption by a cell anomaly undetectable by the spectrometer 6.

There are two ways in which optical interference can be avoided and these are, i) slicing the tissue to a thickness of less than about 20 microns, or ii) ensuring that adjacent light paths through the sample are of different lengths.

Clearly, slicing the tissue to a thickness of less than about 20 microns, typically 4 to 8 microns, can be obtained, for example by microtome sectioning techniques used for histological examination.

Ensuring that adjacent light paths through the sample are of different lengths can be achieved for high pressure spectroscopy by pressing a sample to form the shape of the sample holder described and claimed in co-pending patent application Ser. No. 07/456,351, filed 12/26/89, "An Infrared Absorption Spectra Recording, High Pressure Sample Holder", P. T. T. Wong., now U.S. Pat. No. 4,970,396.

Ensuring that adjacent light paths through the sample are of different lengths can be achieved for non-pressure-dependency spectroscopy by gently pressing a sample to conform to the shape of the cell described in co-pending patent application Ser. No. No. 07/461,182, filed 01/05/90, "A Non-Pressure-Dependency Infrared Absorption Spectra Recording, Sample Cell", P. T. T. Wong, now U.S. Pat. No. 4,980,551.

The tissue samples, if not used directly, can be preserved by freezing and thawing before use.

The detection of infrared absorption spectra can be carried out using, for example, a Fourier transform infrared spectrometer or a grating infrared spectrometer.

Infrared light in the frequency ranges from 1,300 cm$^{-1}$ to 1,800 cm$^{-1}$, and from 2,800 cm$^{-1}$ to 3,050 cm$^{-1}$ have been used to detect cancerous cells in tissue.

Tests have shown that for a neoplasm in a human colon tumor, spectral changes between the neoplasm and healthy tissue cells have been found to exist at frequencies around 1,082 cm$^{-1}$, 1,170 cm$^{-1}$, 1,230 cm$^{-1}$ 1,380 cm$^{-1}$, 1,713 cm$^{-1}$, 2,850 cm$^{-1}$ and 2,960 cm$^{-1}$.

Other test have shown that for a neoplasm in a human liver tumor, spectral changes between the neoplasm and healthy tissue have been found to exist at frequencies around 1,382 cm$^{-1}$, 1,550 cm$^{-1}$, 1,713 cm$^{-1}$, 2,850 cm$^{-1}$ and 2,960 cm$^{-1}$.

Tests to verify the present invention were made using the apparatus described with reference to FIG. 1 and the sample holder described and claimed in co-pending patent application Ser. No. 07/456,351, filed 12/26/89, "An Infrared Absorption Spectra Recording, High Pressure Sample Holder", P. T. T. Wong, now U.S. Pat. No. 4,970,396.

In the tests, a healthy, control tissue sample (not shown) was placed in the sample cell of the sample cell and holder 4 and was exposed to an infrared light beam which had passed through the convex lens 2 from the source 1. The infrared absorption spectrum of the sample was obtained by the infrared spectometer 6. This spectral output was stored in the memory of the computer 8. The same procedure was followed for a tissue sample (not shown) containing neoplasm.

The following examples are typical of the tests that were carried out and illustrate the spectroscopic determination obtained, by the present invention, of differentiating infrared absorption bands for the neoplasms of colon tumors and liver tumors respectively, and different methods for the detection of malignancy made available by the present invention.

More particularly, in the cancer tissues, the following procedures were used.

Samples were obtained from each patient from the tumor itself and from the normal-appearing tissue 5-10 cm away from the tumor, placed in OCT (Optimal Cutting Temperature, Miles Scientific, Napervil, Ill.), frozen in isopentane cooled in liquid nitrogen, and stored at −80° C. until used. Two successive 5 micron thick microtome cuts were obtained. One was used for spectroscopic studies and the other, stained with hematoxylin, was examined histologically by two experienced physicians. The composition of each tissue section was scored blindly as percentage of malignant and normal tissue.

For the spectrographic analysis, small amount (typically 0.01 mg) of tissue or a cell samples were placed at room temperature, together with powdered α-quartz, as an internal pressure calibrant, and a minor amount of $D_2O$, to remove the infrared absorption band of $H_2O$ near the amide I of proteins in a 0.37 mm diameter hole in a 0.23 mm thick stainless steel gasket mounted on a diamond anvil cell.

The results given in the first example were obtained at atmospheric pressure and at increasing, elevated pressures, whereas those given in the other examples were obtained at atmospheric pressure only.

The spectra were measured with a Digilab FTS-60 Fourier transform spectrometer using a liquid nitrogen cooled mercury-cadmium-telluride detector. For each spectrum 256 scans were co-added, at a special resolution of 4 $cm^{-1}$. Frequencies associated with the C=O stretching modes were obtained from third order derivation spectra (Cameron, D. G. et al., Appl. Spectrosc. 41: 539–544, 1987), using a breakpoint of 0.3 in Fourier domain. Pressures at the sample were determined from the 695 $cm^{-1}$ infrared absorption band of α-quartz (see P. T. T. Wong D. J. Moffatt and F. L. Baudais, Appl. Spectroscopy, 39: pp. 733–735, 1985).

Samples were obtained from nine patients who underwent partial bowel resection for colorectal cancer. The samples were obtained immediately following the bowel resection. Table I below described pertinent clinical features of this group of patients. Staging of tumors using the modified Duke's classification (Astler, V. B. et al., Ann. Surg. 39: 864, 1954) showed that the patients were either stage B2 (the tumor penetrated the bowel wall but did not involve lymph nodes) or stage C (lymph nodes involved).

TABLE I

| Patient | | | | Tumor | | | Histology of tissue section (percent) | |
|---|---|---|---|---|---|---|---|---|
| No. | sex | race | age | location | size, cm | stage | cancer | normal |
| 1 | M | W | 73 | rectum | 1.5 × 3 | C | 50 | 30* |
| 2 | F | W | 79 | ascending | 2 × 3 | B2 | 10 | 90 |
| 3 | F | W | 79 | ascending | 3.5 × 3 | B2 | 33 | 66 |
| 4 | M | W | 54 | sigmoid | 3 × 3 | C | 20 | 80 |
| 5 | M | O | 48 | rectum | 3.5 × 3 | B2 | 50 | 50 |
| 6 | M | W | 82 | rectum | 3 × 3 | C | 10 | 90 |
| 7 | M | W | 70 | sigmoid | 2.5 × 2 | C | 60 | 40 |
| 8 | M | W | 67 | sigmoid | 2 × 3 | C | 40 | 60 |
| 9 | M | W | 70 | sigmoid | 3 × 3 | C | 40 | 60 |

*20% was adenoma (benign)

Figure 2:
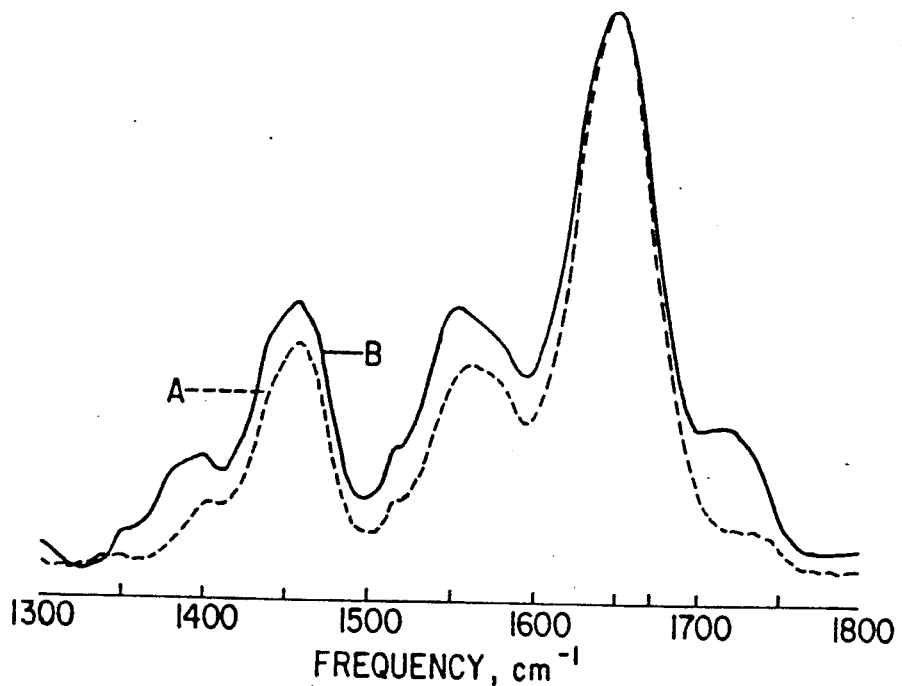
FIG. 2 shows infrared spectra in the frequency range 1,300 to 1,800 cm$^{-1}$, obtained on tissue sections from a colon tumor histologically determined to be 10% cancerous and from histologically normal colonic mucosa.

Typical spectra are shown in FIG. 2 wherein the spectrum designated A, and shown - - -, denotes results on tissue samples taken from an area outside the neoplasm which has been determined to be histologically normal and the spectrum designated B, and shown ——, denotes tissue samples found histologically to be 10% malignant (Spectra are from Patient No. 2). Consideration of these and spectra from samples from the other patients indicate that the intensity at 1380 $cm^{-1}$ and 1,713 $cm^{-1}$ is increased in all samples of colon cancer tissue as compared to the control tissue. The finding of increased intensity at 1,380 $cm^{-1}$ and 1,713 $cm^{-1}$ for malignancy containing samples was true for all nine pairs of malignant and normal colonic tissue.

The increase in intensity at 1,713 $cm^{-1}$ in the colon cancer tissue was due to an increase in a specific membrane lipid concentration.

Figure 3:
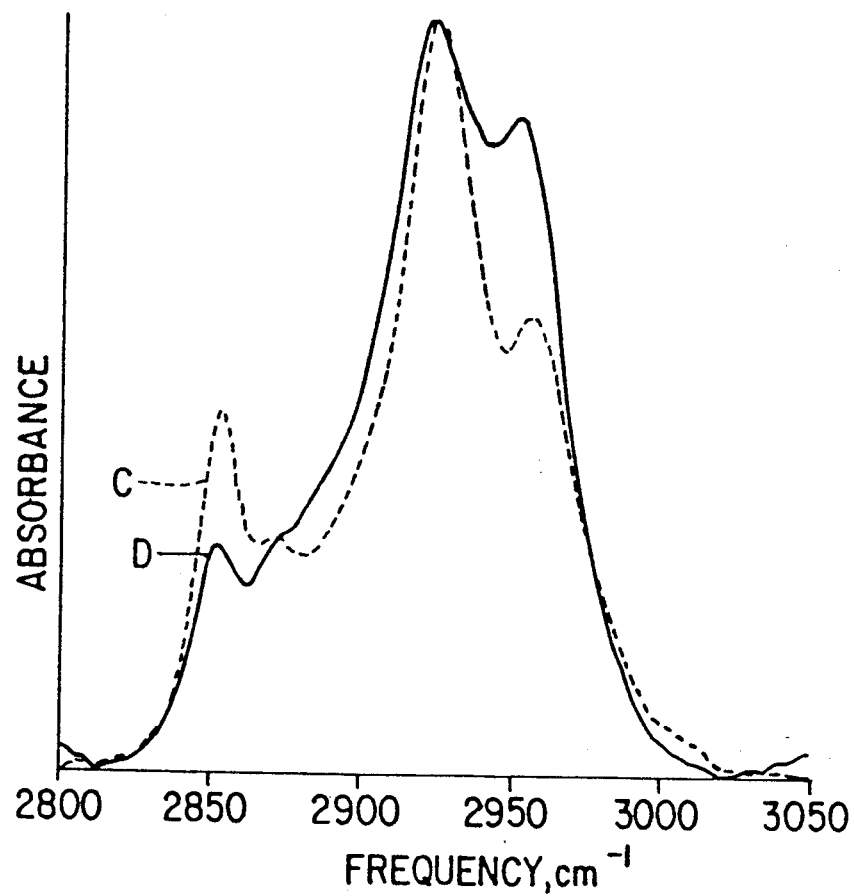
FIG. 3 shows infrared spectra in the frequency range 2,800 to 3,050 cm$^{-1}$, obtained on tissue sections from a colon tumor histologically determined to be 50% cancerous and from histologically normal colonic mucosa.

FIG. 3 shows infrared spectra in the range of 2,800 $cm^{-1}$ to 3,050 $cm^{-1}$. The spectrum designated D; and shown ——, is from the normal healthy tissue samples and the spectrum designated C, and shown - - -, is from the tissue sample found histologically to be 50% malignant (from patient No. 5). In going from the normal healthy tissue samples to the malignant tissue sample, the intensity of the band near 2,960 $cm^{-1}$ decreases, due to an decrease in the malignant tissue sample in $CH_3$ groups whereas that of the band near 2,850 $cm^{-1}$ increases, due to increase in $CH_2$ groups, which may be in membrane lipids.

Figure 4:
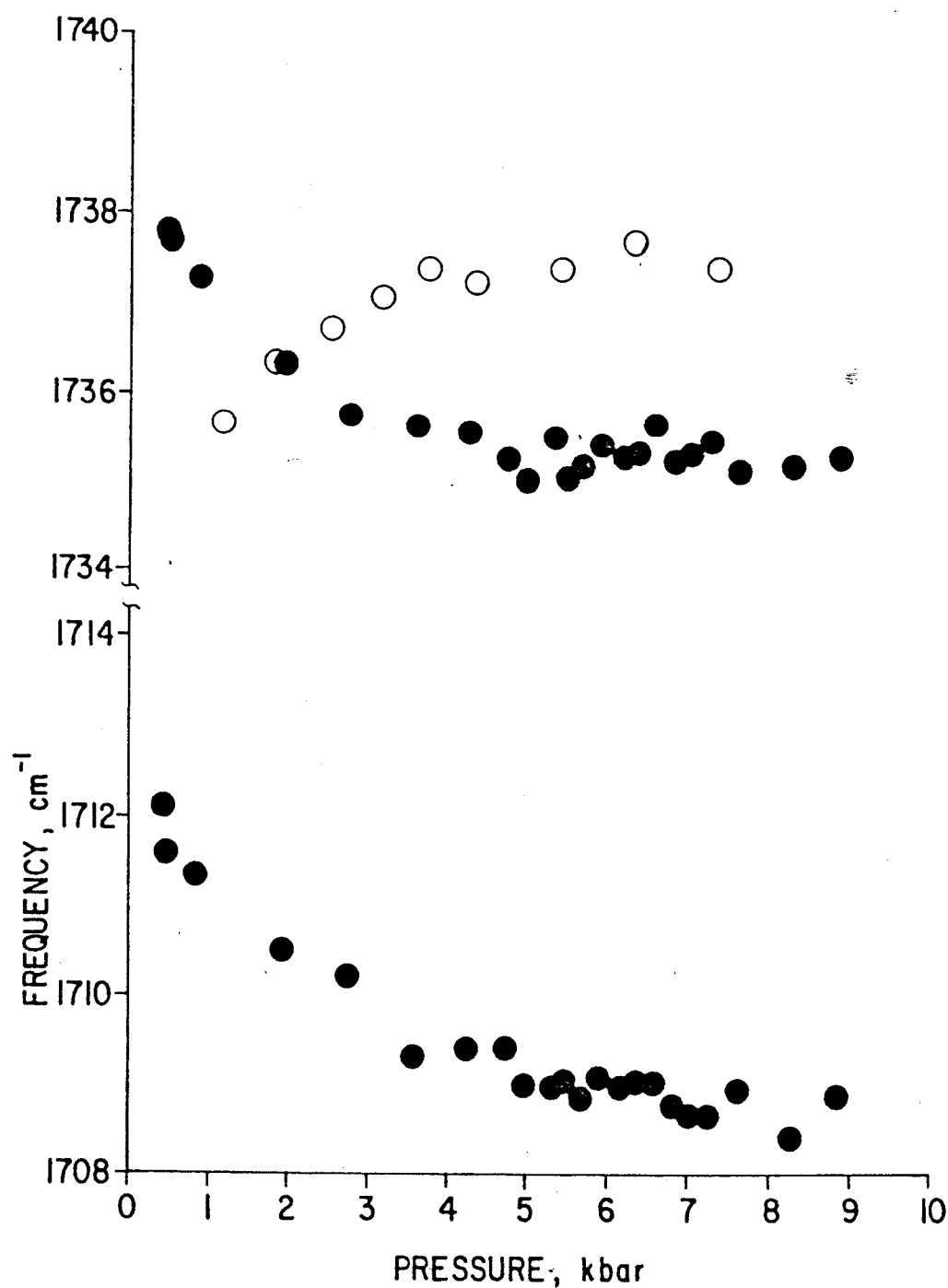
FIG. 4 shows a comparison of the pressure dependencies of C=O stretching frequencies of infrared spectra of a healthy colonic tissue sample with that of a malignant colonic tissue taken from the same patient.

FIG. 4 shows the pressure dependencies of infrared frequencies of the infrared bands near 1,713 $cm^{-1}$ and 1,738 $cm^{-1}$ for the same tissue samples described in FIG. 2.

In FIG. 4,

○ denotes test results from the normal healthy tissue samples, and

● denotes test results from the malignant tissue samples.

In the infrared spectra for the malignant tissue samples, see for example FIG. 2, the 1,713 $cm^{-1}$ band contains a shoulder on the side of higher frequencies which can be resolved into a well defined band near 1,738 $cm^{-1}$ in the third order derivative spectra (see D. G. Cameron et al., Appl. Spectroscopy, 41, pp. 539–544, 1987). In the infrared spectra of the normal healthy tissue sample, only one weak band at around 1,736 $cm^{-1}$ is observed, which is too weak to be resolved into two bands in the third order derivative of the spectra, as is shown possible for the malignant tissue samples. The frequencies of both the third order derivative bands for the malignant tissue samples are shown to decrease with increasing pressure, whereas the frequencies of the single weak band for the normal healthy tissue samples is shown to increase with increasing pressure in some instances and decrease with increasing pressure in order instances.

Hepatoma tissue samples for diagnosis were obtained from three patients and compared with healthy tissue samples from 5 patients with normal livers.

Figure 5:
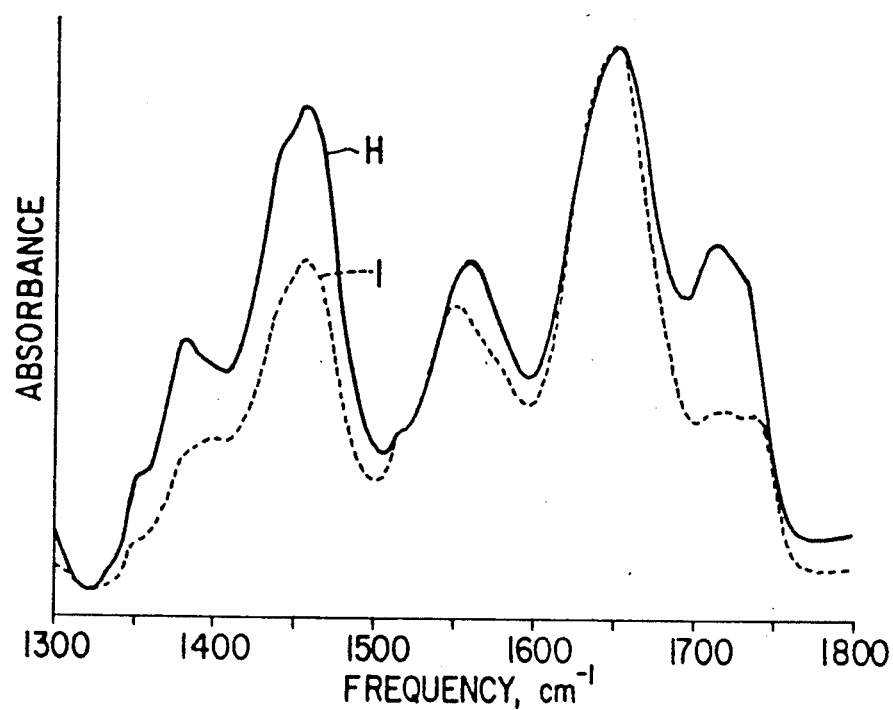
FIG. 5 shows infrared spectra obtained on tissue sections from a liver tumor histologically determined to be cancerous and another one histologically normal hepatic tissue.

FIG. 5 shows infrared spectra, and H shown —— denotes hepatoma tissue samples, and I shown - - - denotes normal healthy liver tissue samples.

These results, together with those from other patients, show increased infrared intensity at infrared bands near 1,382 $cm^{-1}$ and 1,713 $cm^{-1}$, and a frequency shift at an infrared band near 1,550 $cm^{=1}$.

From these tests it will be seen that the information stored in the computer 8 can then can analyzed by one or more of the following procedures;

(1) The infrared spectra from control tissue samples and cancerous tissue samples in either of the frequency regions ranges of 1,300 $cm^{-1}$ to 1,800 $cm^{-1}$ (FIG. 2) or 2,800 $cm^{-1}$ to 3,050 $cm^{-1}$ (FIG. 3) can be simultaneously displayed and plotted by the readout 10. The presence of cancerous tissue cells in the cancerous tissue sample can then be determined by visual comparison of the differences in the spectra displayed for the control samples to those of the cancerous tissue samples.

(2) The infrared intensity of the amide I band at a frequency of around 1,650 $cm^{=1}$ of the overall proteins is about the same for a normal healthy tissue sample as it is for a malignant tissue sample (FIGS. 4 and 5). Therefore, the intensity of the amide I infrared band can be used internally in the computer as an infrared absorption intensity standard. Thus, the infrared intensity ratio between a cancerous tissue sample at the infrared band near 1,713 cm$^{-1}$ (FIGS. 2 and 5) and that of the amide I band or that between the infrared band near 1,380 cm$^{-1}$ and that of the amide I band can be calculated and compared by the computer 8 with the infrared intensity ratios obtained from normal healthy tissue samples. These two infrared intensity ratios will be greater for cancerous tissue samples than those for normal healthy tissue samples and can be displayed by the readout 10.

(3) The peak height ratio between the infrared intensities at frequency bands near 2,960 cm$^{-1}$ and 2,850 cm$^{-1}$ (FIG. 3) may be calculated by the computer 8. This ratio is smaller for cancerous tissue samples compared to normal tissues.

(4) The peak frequencies of the infrared band near 1,550 cm$^{-1}$ for both normal healthy tissue samples and those of hepatoma tissue samples are calculated and compared by the computer 8. This frequency is greater for hepatoma tissue samples than for normal healthy tissue samples and so this difference can be obtained from the readout 10 as an indication of the presence of hepatoma in a tissue sample.

(5) When the known infrared, spectroscopic, pressure tuning technique is used, the test procedure is also simplified in that only cancerous tissue samples need to be examined. A sample to be tested is placed in the sample holder described and claimed in co-pending patent application Ser. No. 07/456,351, filed 12/26/89, "An Infrared Absorption Spectra Recording, High Pressure Sample Holder", P. T. T. Wong, now U.S. Pat. No. 4,970,396 and mounted in the apparatus described with reference to FIG. 1. Two infrared spectra of the same tissue sample are then measured; one at atmospheric pressure and the other at high pressure in the range, for example, of 1 to 10 kbars. The frequencies of the infrared band near 1,713 cm$^{-1}$ in these two spectra are calculated and compared by the computer 8. For a cancer cell containing sample the frequency of this band is much lower at high pressure than at atmospheric pressure.

Tissue or cell anomalies which may be detected according to the present invention include, for example, infectious and non-infectious, diseases, where infrared absorption occurs in the sample, at at least one range of frequencies, due to the vibration of at least one functional group of molecules being present in a sample which is characteristic of that tissue or cell anomaly. This can be determined by routine tests and the functional group of molecules detected may, for example be from cell membranes, lipids, proteins or nucleic acids.

Typical non-infectious diseases are cancer, diabetes, cirrhosis and arthritis.

Examples of the kinds of tissue or cells, which may be neoplastic, in which the presence, of abnormality, e.g. malignancy, can be detected, according to the present invention include colorectal tumors (for detecting colon carcinoma), liver tumors (for detecting hepatoma), and other cancerous as well as neoplastic cells in blood.

Figure 6:
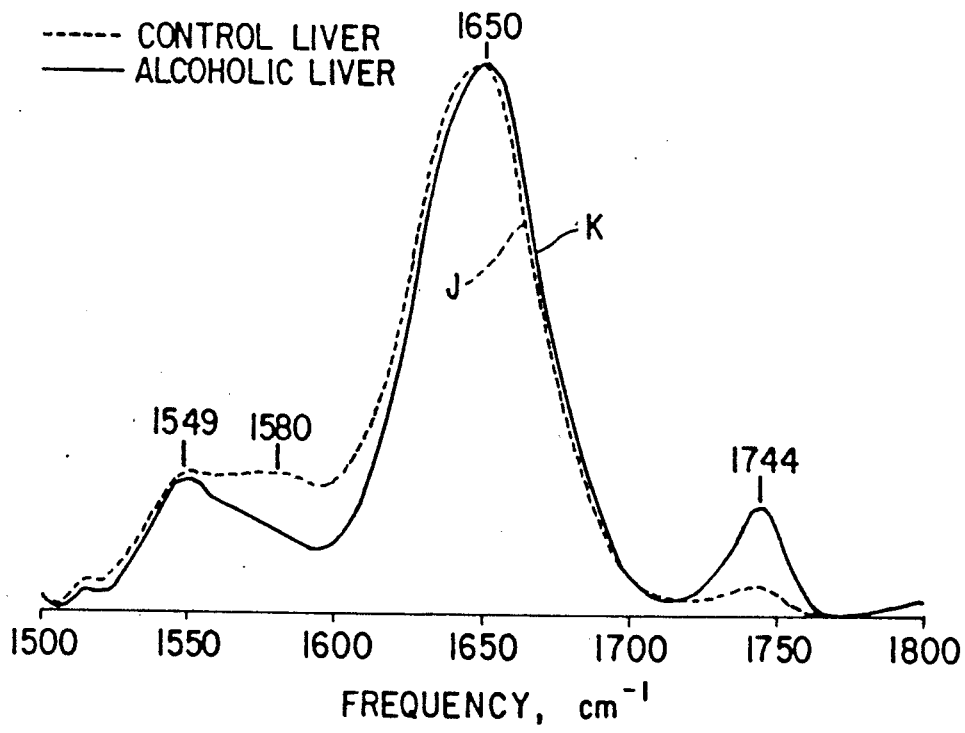
FIG. 6 shows infrared spectra in the range 1,500 to 1,800 cm$^{-1}$, obtained on tissue sections from rat alcoholic liver and normal rat liver.

FIG. 6 shows infrared spectra, and J shown - - - is for natural healthy rat liver tissue samples, and K shown —— is for alcoholic rat liver.

These results show increased infrared intensity for alcoholic rat liver tissue at the infrared band near 1,744 cm$^{-1}$, decreased intensity at frequency bands near 1,549 cm$^{-1}$ and 1,580 cm$^{-1}$ and a frequency shift at infrared bands near 1,650 cm$^{-1}$, all of which are indications of the presence of cirrhosis in the alcoholic liver tissue samples and are due to the accumulation of triglycerides and side chain binding changes in the protein.

Figure 7:
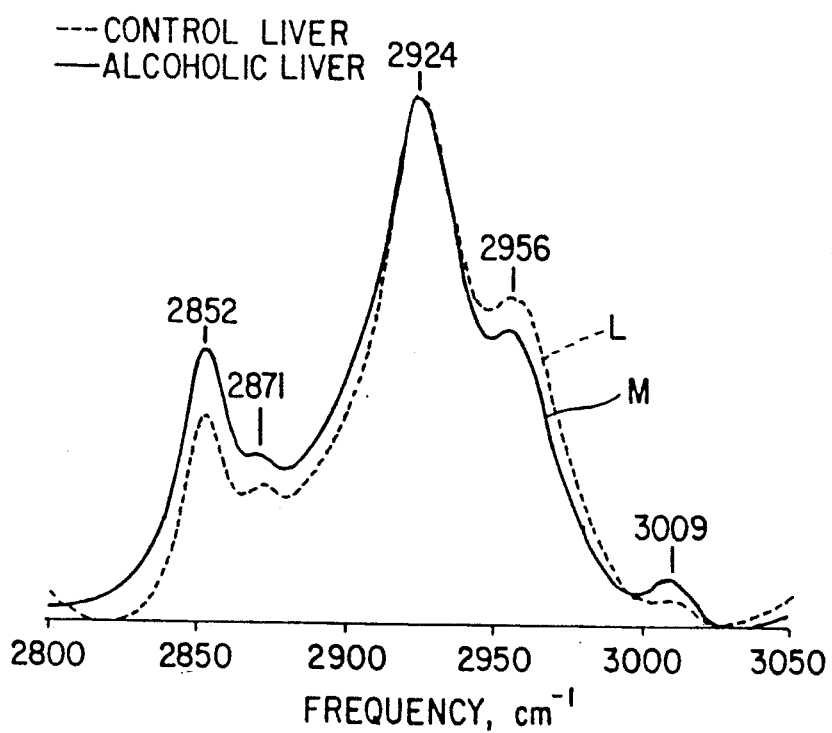
FIG. 7 shows infrared spectra in the range 2,800 to 3,050 cm$^{-1}$ obtained on tissue sections from rat alcoholic liver and normal rat liver.

FIG. 7 shows infrared spectra, and L shown - - - is for natural healthy rat liver tissue, and M shown —— is for alcoholic rat liver tissue.

These results show increased infrared intensity for alcoholic rat liver tissue at infrared bands near 2,852, 2,871, and 3,009 cm$^{-1}$ and decreased infrared intensity for alcoholic rat liver tissue at the infrared band near 2,956 cm$^{-1}$, all of which are indications of the presence of cirrhosis in the alcoholic liver tissue samples due to the presence of less methyl branches in lipids and more unsaturated lipids therein.

Figure 8:
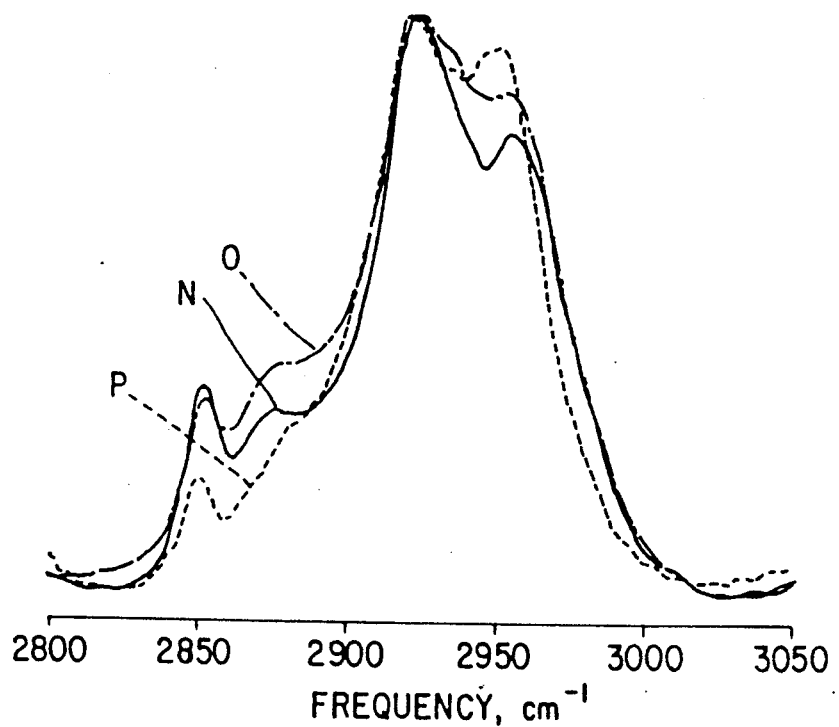
FIG. 8 shows infrared spectra in the range 2,800 to 3,050 cm$^{-1}$ obtained on tissue sections of thymus disease tissue at 0, 5 and 45 hours at room temperature.

FIG. 8 shows infrared spectra, and N shown —— is for normal thymus tissue sample immediately after being removed from a patient O shown — - is for normal thymus tissue sample after 5 hours at room temperature, and P shown - - - is for normal thymus tissue sample after 45 hours at room temperature, all from the same patient.

The results show increased infrared intensity at the infrared bands near 2,960 cm$^{-1}$ while a decrease is shown at infrared bands near 2,850 cm$^{-1}$ with increasing time at room temperature indicating the amount of lipids containing branched fatty acids increases.

Figure 9:
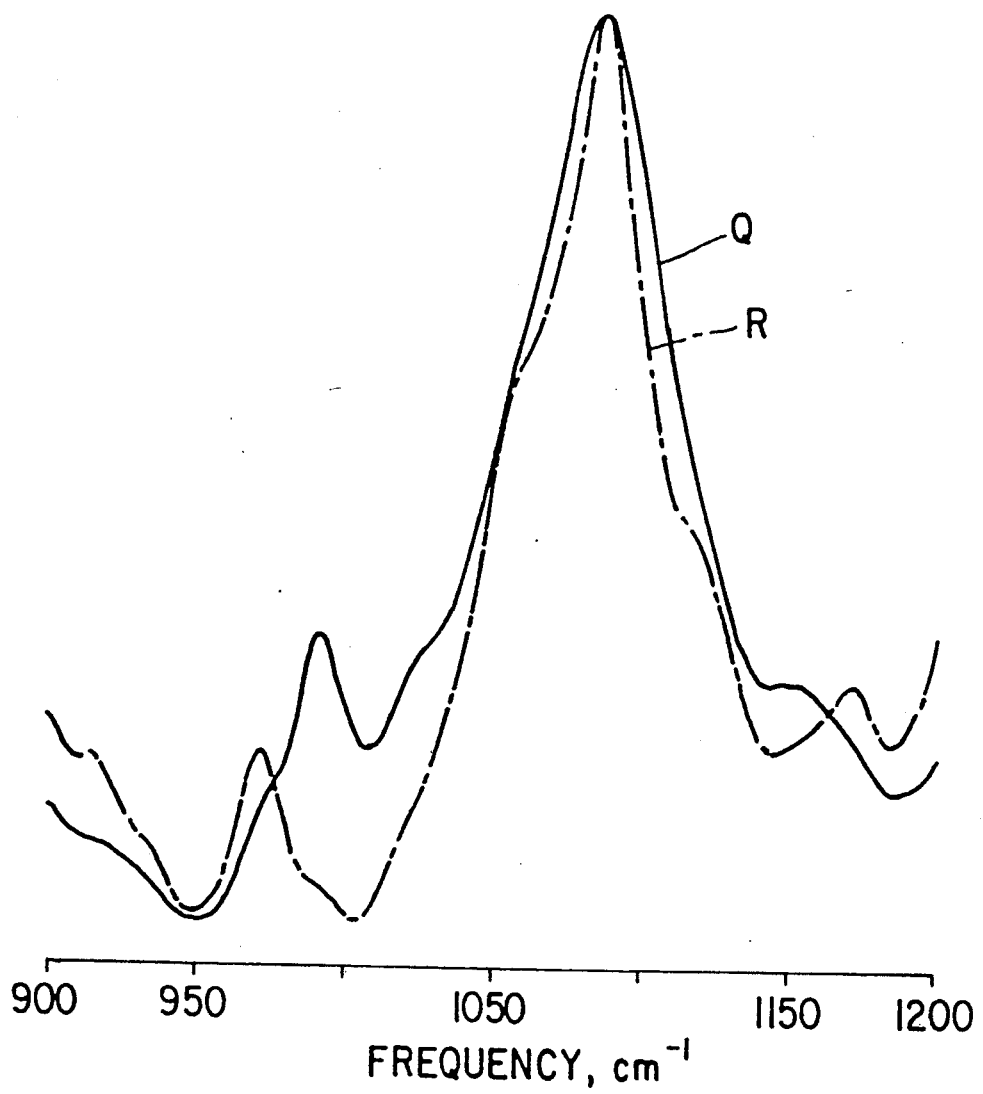
FIG. 9 shows infrared spectra in the range 900 to 1,200 cm$^{-1}$ obtained on cultured human colon epithelial cells and cultured normal human colon fibroblasts.

FIG. 9 shows infrared spectra, and Q shown —— is for cultured normal human colon fibroblasts, and R shown — - is for cultured human epithelial cells.

The results show that frequency of the infrared band decreases from near 990 cm$^{-1}$ for normal cells to near 973 cm$^{-1}$ for epithelial cells, while the reverse occurs for the infrared band near 1,154 cm$^{-1}$ for normal cells in that there is no increase to 1,168 cm$^{-1}$ for epithelial cells.

it is within the scope of the present invention for the determination of the infrared absorption of be carried out in any known manner, such as, for example, i) from optical interference free transmittance characteristics of the sample, or ii) from the attenuated reflectance characteristics of the sample.

It has also been proposed in "High-Pressure Infrared Spectroscopy Study of Human Proinsulin Gene Expression in Live Escherichia Coli Cells", P. T. T. Wong, D. M. Zahab, S. A. Narang and W. L. Sung, Biomedical and Biophysical Research Communications, vol. 146, No. 1 July 15, 1987, pp. 232-238, to monitor the production of recombinant proteins in *E. Coli* using high-pressure infrared spectroscopy to observe the effects of pressure on specific spectral parameters due to the vibrational modes of the skeletal amide groups of bacterial proteins. A person skilled in the art on reading this article would not be led to believe that anomalies present in tissue samples can be detected using infrared spectroscopy.

Step (b) of the method of the invention mentioned hereinbefore is directed to determining, by spectroscopic analysis, whether variation in infrared absorption occurs in the sample at at least one range of frequencies, due to the vibration of at least one functional group of molecules present in the sample which is characteristic of the anomaly. In the art of spectroscopic analysis at frequencies in the infrared region, the absorption bands are known to result from the energy consumed by initiating vibrations in functional groups within molecules. Different groups have specific frequencies at which this absorption is a maximum. The routine tests that can be used to determine variations characteristic of an anomaly can comprise, for example, preparing normal tissue samples and samples containing anomalous tissue and identifying the distinguishing features of the spectra that result from known differences detected in the samples by other procedures such as microscopy. It will be appreciated that, in order to practice the present inventions, it is not necessary to known the chemical nature of the functional groups of molecules present in samples which is characteristic of the anomaly, even though this can be done by routine tests.

Patent application Ser. No. 07/456,351, filed 12/26/89, "An Infrared Absorption Spectra Recording, High Pressure Sample Holder", P. T. T. Wong, now U.S. Pat. No. 4,970,396 referred to hereinbefore is incorporated herein by reference.

Patent application No. 07/461,182, filed 01/05/90, "Non-Pressure-Dependency Infrared Absorption Spectra Recording, Sample Cell," P. T. T. Wong, now U.S. Pat. No. 4,980,551 referred to hereinbefore is incorporated herein by reference.

We claim:

1. A method of detecting the presence of anomalies in biological tissue or cells in natural or cultured form by infrared spectroscopy, comprising:
   a) directing a beam of infrared light at a sample of the tissue or cells in natural or cultured form, and
   b) determining, by spectroscopic analysis, whether variation in infrared absorption occurs in the sample, at at least one range of frequencies, due to the vibration of at least one functional group of molecules present in the sample which is characteristic of that anomaly.

2. A method according to claim 1, wherein the anomaly is a tissue or cell anomaly.

3. A method according to claim 2, wherein the anomaly is in neoplastic tissue or cells.

4. A method according to claim 1, wherein the beam of infrared light is passed through the samples in an optical interference free manner, and the infrared absorption is determined by the transmittance characteristics of the sample.

5. A method according to claim 4, wherein the spectroscopic analysis is carried out with the sample subjected to high pressure to render readily detectable the infrared absorption characteristics of the said at least one functional group.

6. A method according to claim 1, wherein the spectroscopic analysis is carried out by subjecting the sample to at least two difference pressures to render the infrared absorption characteristic detectable by frequency shift.

7. A method according to claim 1, wherein the spectroscopic analysis is carried out by subjecting the sample to at least two different pressures to render the infrared absorption characteristic detectable by intensity change.

8. A method according to claim 3, wherein the said at least one functional group is a $CH_3$ group.

9. A method according to claim 3, wherein the said at least one functional group is a $C=O$ group.

10. A method according to claim 9, wherein the $C=O$ group is in a membrane lipid.

11. A method according to claim 3, wherein the said at least one functional group is a $CH_2$ group.

12. A method according to claim 1, wherein the tissue is liver tissue and the said anomaly is an indication of cirrhosis in the liver tissue.

13. A method according to claim 1, wherein the tissue is thymus tissue, and the said anomaly is an indication of the length of time that has passed since that thymus tissue was removed from a patient.

14. A method according to claim 1, wherein the cells are human colon epithelial cells.

15. A method according to claim 1, wherein the tissue is colon tumor tissue and the said anomaly is an indication of malignancy in the said tissue.

16. A method according to claim 1, wherein the tissue is liver tumor tissue and the said anomaly is an indication of malignancy in the said tissue.

* * * * *